Figure 1A:
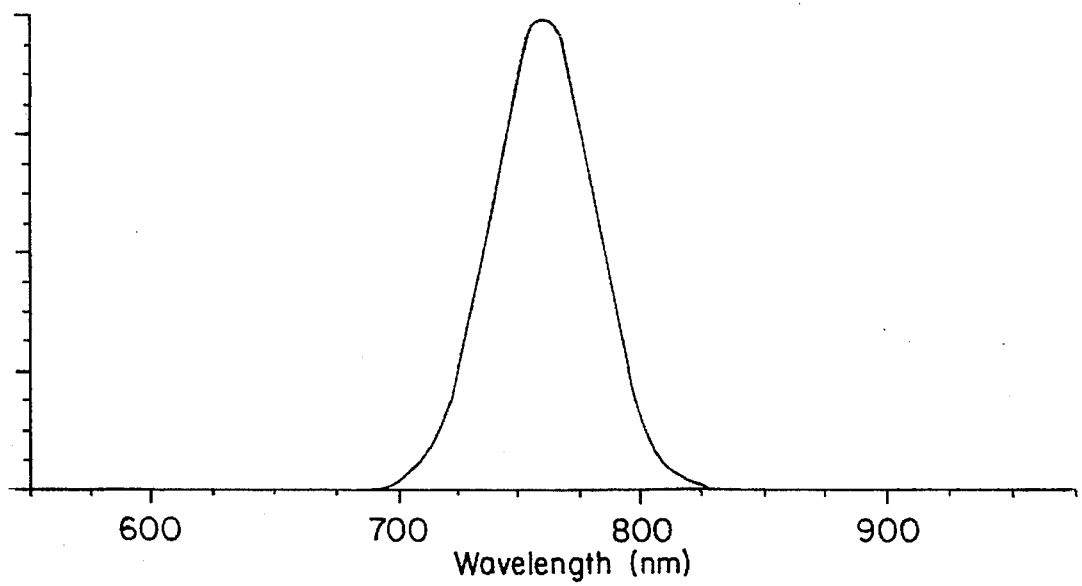

United States Patent [19]

Hanning

[11] Patent Number: 5,641,640
[45] Date of Patent: Jun. 24, 1997

[54] METHOD OF ASSAYING FOR AN ANALYTE USING SURFACE PLASMON RESONANCE

[75] Inventor: Anders Hanning, Sollentuna, Sweden

[73] Assignee: Biacore AB, Uppsala, Sweden

[21] Appl. No.: 360,811

[22] PCT Filed: Jun. 29, 1993

[86] PCT No.: PCT/SE93/00589

§ 371 Date: Dec. 29, 1994

§ 102(e) Date: Dec. 29, 1994

[87] PCT Pub. No.: WO94/00751

PCT Pub. Date: Jan. 6, 1994

[30] Foreign Application Priority Data

Jun. 29, 1992 [SE] Sweden .................................. 9201984

[51] Int. Cl.$^6$ .......................... G01N 33/552; G01N 33/53
[52] U.S. Cl. .......................... 435/7.92; 385/12; 385/129;
385/130; 356/313; 356/318; 356/445; 422/82.05;
422/82.08; 422/82.11; 435/7.9; 435/7.93;
435/7.94; 435/808; 436/164; 436/165; 436/518;
436/524; 436/525; 436/527; 436/805
[58] Field of Search .......................... 385/12, 129, 130;
356/317, 318, 445; 422/82.05, 82.08, 82.11;
435/7.9, 7.92–7.94, 808; 436/164, 165,
518, 524, 525, 527, 805

[56] References Cited

U.S. PATENT DOCUMENTS 4,954,435  9/1990  Krauth .

FOREIGN PATENT DOCUMENTS

| 0276142 | 7/1988 | European Pat. Off. . |
| 0326291 | 8/1989 | European Pat. Off. . |
| 0341927 | 11/1989 | European Pat. Off. . |
| WO90 05295 | 5/1990 | WIPO . |
| 9011525 | 10/1990 | WIPO . |
| WO93 04357 | 3/1993 | WIPO . |

OTHER PUBLICATIONS

Assay Method Using Surface Plasmon Resonance Spectrometry Biosensors & Bioelectronics 6(1991), pp. 215–225 "Principles and Sensitivities of Integrated Optical . . . ".
Pockrand et al, J. Opt. Soc. Am., vol. 68, No. 8, pp. 1147–1151 (Aug. 1978).
Pockrand et al, J. Chem. Phys., 69(9), pp. 4001–4011 (Nov. 1,1978).
Wähling et al, Z. Naturforsch, 33a, pp. 907–909 (1978).
Wähling et al, Z. Naturforsch, 36a, pp. 588–594 (1981).
Van Gent et al, J. Chem. Soc., Chem. Commun., pp. 893–895 (1988).
Van Gent et al, Sensors and Actuators A. 25–27, pp. 449–452 (1991).
Van Gent et al, Sensors and Actuators, 17, pp. 297–305 (1989).

*Primary Examiner*—Christopher L. Chin

[57] ABSTRACT

In a method of assaying for an analyte in a fluid sample, the presence of the analyte is detected by determining the resulting change in refractive index at a solid optical surface in contact with the sample, which change is caused by the analyte involving or influencing the binding or release of a refractive index enhancing species to or from, respectively, the optical surface, the refractive index of the refractive index enhancing species varying with wavelength. According to the invention, the determination comprises determining the variation with wavelength of the resulting change of refractive index, caused by the variation of refractive index with wavelength of the refractive index enhancing species, for a number of discrete wavelengths or for a continuous range of wavelengths. This variation is representative of the amount of analyte.

14 Claims, 2 Drawing Sheets

METHOD OF ASSAYING FOR AN ANALYTE USING SURFACE PLASMON RESONANCE

The present invention relates to an improvement in assays of the type wherein the presence of the analyte is detected by determining a change in refractive index at a solid optical surface, which change is caused by the analyte involving or influencing the binding of a refractive index enhancing species to the optical surface, or the release therefrom, respectively.

One type of method for determining such refractive index changes at an optical surface is based upon surface plasmon resonance, hereinafter SPR. The phenomenon of SPR is well known. In brief, SPR is observed as a dip in intensity of light reflected at a specific angle from the interface between an optically transparent material, e.g. glass, and a thin metal film, usually silver or gold, and depends on among other factors the refractive index of the medium (e.g. a sample solution) close to the metal surface. A change of refractive index at the metal surface, such as by the adsorption or binding of material thereto, will cause a corresponding shift in the angle at which SPR occurs. To couple the light to the interface such that SPR arises, two alternative arrangements are used, either a metallized diffraction grating (Wood's effect), or a metallized glass prism or a prism in optical contact with a metallized glass substrate (Kretschmann effect). For further details on SPR, reference is made to our WO 90/05295. In an SPR-based immunoassay, a ligand may be bound to the metal surface, and the interaction thereof with an analyte of an aqueous sample in contact with the surface is monitored.

SPR assays have, however, certain fundamental limitations which restrict the technical performance thereof. One major limiting factor is the sensitivity, or signal strength. The SPR response depends on the volume and refractive index of the bound analyte, which volume is limited by mass transfer, reaction-kinetic and equilibrium parameters. For example, water and diluted aqueous buffers have a refractive index of about 1.33, whereas most proteins have a refractive index in the region of about 1.5 to 1.6. Since the SPR-measurement response is proportional to the change in refractive index caused when e.g. protein molecules are adsorbed to the surface and displace water therefrom, the refractive index difference between the protein and the buffer solution puts a theoretical limit to the strength of response that may be obtained. It is thus understood that SPR-based immunoassays for substances of low molecular weight or occurring in low concentrations, like, for instance, haptens, are problematic due to the very small changes in refractive index caused when the analyte binds to or dissociates from the antibody-coated sensing surface.

Another limiting factor is non-specific binding to the sensing surface, a problem common to all types of direct-measuring sensors, i.e. where no labelled reagent, such as an enzyme or a fluorophore, is used to provide the detected signal. Since SPR generates a signal for all material bound to the surface, the analyte can not be distinguished from non-specific material.

Still another limiting factor is the variation of the refractive index with temperature. The temperature difference between the base line reading and the reading of analyte uptake therefore puts a theoretical limit to the minimum amount of analyte that may be detected. Also other parameters than temperature, e.g. mechanical or chemical disturbances, that may vary between the time of the baseline reading and the reading of the analyte uptake will, of course, affect the measuring response.

Further limitations are, for example, non-ideal optics as well as electronic and other baseline fluctuations.

More or less unsuccessful attempts to avoid the sensitivity or signal strength problem are described in EP-A-276 142 and WO 90/11525 (the former specifically making use of the above mentioned Wood's effect, and the latter of the Kretschmann effect). Both publications disclose the conjugation of a reagent (for example the analyte or an analyte analogue in a competition assay) with a refractive index increasing species or probe. Such a probe may, for instance, be a molecule or particle having a high refractive index and/or a large size, such as a heavy metal ion, a polycyclic aromate or dye, or ferritin.

The major reason for the above attempts being unsuccessful resides in the fact that among organic species it is difficult to find molecules having a refractive index higher than about 1.6–1.7. Inorganic species, on the other hand, may have refractive indices of about 2–3, but instead they may be difficult to combine chemically with proteins. The possibilities of significantly enhancing the SPR-signals as proposed by the two cited publications are therefore rather limited, unless, of course, extremely large and thereby impractical probes are used.

A more successful solution to the sensitivity problem is provided in our international patent publication No. WO 93/04357 (the entire disclosure of which is incorporated herein by reference) which discloses and claims a method of increasing the sensitivity of SPR and related assays based upon the measurement of refractive index changes at a sensing surface, utilizing the fact that the refractive index is highly dependent on the wavelength. Whereas, for most substances, the refractive index decreases very slowly with increasing wavelength within the visible and near infrared region (normal dispersion), it varies heavily in the vicinity of resonance wavelengths, i.e. at light absorption peaks, a phenomenon called anomalous dispersion. In this region the refractive index is roughly a function of the negative derivative of the absorptivity (extinction coefficient) with respect to the wavelength. Thus, at a slightly higher wavelength than the resonance wavelength, the refractive index reaches a maximum, i.e. where the negative derivative of the absorptivity has its maximum. According to our above-mentioned international patent application WO 93/04357, a considerable increase in sensitivity is therefore obtained by matching the measurement wavelength with the absorptivity maximum of the refractive index enhancing species used in the particular assays, preferably a dye or chromophoric molecule, and more specifically such that the measurement wavelength substantially corresponds to the maximum of the negative derivative of the absorptivity with respect to the wavelength. This may be accomplished either by selecting the index enhancing species to conform with the measuring wavelength of a particular instrument or application, or by selecting the measuring wavelength to conform with a specific index enhancing species.

It may in this context be mentioned that SPR studies of organic dyes had been described in the prior art before the priority date of our afore-mentioned international application WO 93/04357. For example, Pockrand et al. report in J. Opt. Soc. Am. 68(8) (1978) 1147 and J. Chem. Phys. 69(9) (1978) 4001 studies of Langmuir-Blodgett films of N,N'-di (methyloctadecyl)-squarylium and N,N'-dioctadecyloxacarbocyanine on silver surfaces. Roughly, they found the maximum refractive index of the chromophoric parts of the molecule to be 3–4, while the minimum refractive index was near zero.

Wähling et al., Z. Naturforsch., 33a (1978) 907 and Z. Naturforsch., 36a (1981) 588, studied monolayers of the dye "S-120" on silver surfaces at different wavelengths.

J. van Gent et al., J. Chem. Soc. Chem. Comm., (1988), 893, Sensors and Actuators, 17 (1989) 297, and Sensors and Actuators, 25–27 (1991) 449, disclose studies with SPR-sensors having surface-immobilized dyes, the latter changing their absorptivity spectrum and thereby their refractive index spectrum upon the uptake of analyte, for example, ammonia, protons or metal ions.

While the sensitivity in SPR assays has been considerably improved by the invention disclosed in our international patent application WO 93/04357, the other problems in SPR assay mentioned above still remain.

The object of the present invention is therefore to provide an assay method based upon the measurement of a change in refractive index at an optical surface, particularly an SPR assay, which method in addition to having a considerably increased sensitivity also overcomes the other above mentioned major limitations of SPR and related methods.

In accordance with the present invention, this is achieved by, as in our international patent application WO 93/04357, utilizing the anomalous behaviour of the refractive index variation with the wavelength (which variation is usually called dispersion), i.e. that the refractive index exhibits a strong maximum at a wavelength slightly higher than the absorption peak, and a minimum at a slightly lower wavelength than the absorption peak. However, instead of measuring the refractive index change at one, discrete high refractive index wavelength as in our copending application, the present invention proposes to measure the variation of the change of the refractive index with wavelength for a number of, i.e. at least two, discrete wavelengths or a continuous wavelength range, which variation is caused by the variation of the refractive index with wavelength of the refractive index enhancing species. Generally, this measured variation should, of course, be as high as possible.

By such measurement of the refractive index variation at two or more discrete wavelengths or in a continuous wavelength range, a direct-measuring method like, for example, SPR, is in practice converted into an indirect method, i.e. a measuring principle corresponding to e.g. fluorescence or enzyme immunoassays is obtained. Thereby only the "label" is detected and not other material, including non-specifically bound material, meaning that a considerable increase in selectivity is obtained.

Thus, in accordance with the present invention there is provided a method of assaying for an analyte in a fluid sample, wherein the presence of the analyte is detected by determining the resulting change in refractive index at a solid optical surface in contact with the sample, which change is caused by the analyte involving or influencing the binding or release of a refractive index enhancing species to or from, respectively, the optical surface, the refractive index of said refractive index enhancing species varying with wavelength. The method is characterized in that the determination comprises determining the variation with wavelength of said resulting change of refractive index, caused by the variation of refractive index with wavelength of the refractive index enhancing species, for a number of discrete wavelengths or for a continuous range of wavelengths, said variation being representative of the amount of analyte.

The terms "assay" and "analyte" are to be interpreted in a broad sense, the method of the invention thus being meant to encompass the detection or monitoring of any substance or species for any purpose whatsoever.

In a preferred embodiment of the invention, hereinafter referred to as the differential method, the variation measured is the refractive index difference between the refractive indices measured at two different wavelengths. Preferably, one measuring wavelength is selected at or near the refractive index maximum, i.e. at or near the maximum of the negative derivative of the absorptivity with respect to wavelength of said refractive index enhancing species. The other measuring wavelength should preferably be at or near the refractive index minimum plateau, as will be explained below, i.e. in the vicinity of the maximum of the derivative of the absorptivity with respect to wavelength of said refractive index enhancing species.

The advantages of the invention will be better understood from the following discussion of the beneficial influence of the invention (using the above described differential method) upon the above mentioned shortcomings or limitations of SPR assays.

Figure 1B:
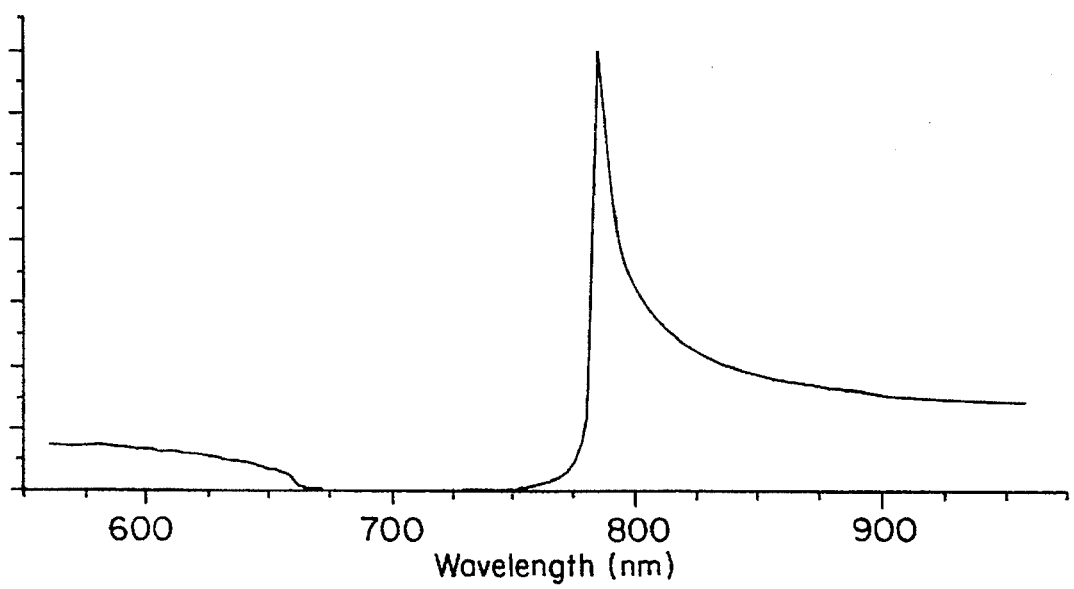
Figure 2:
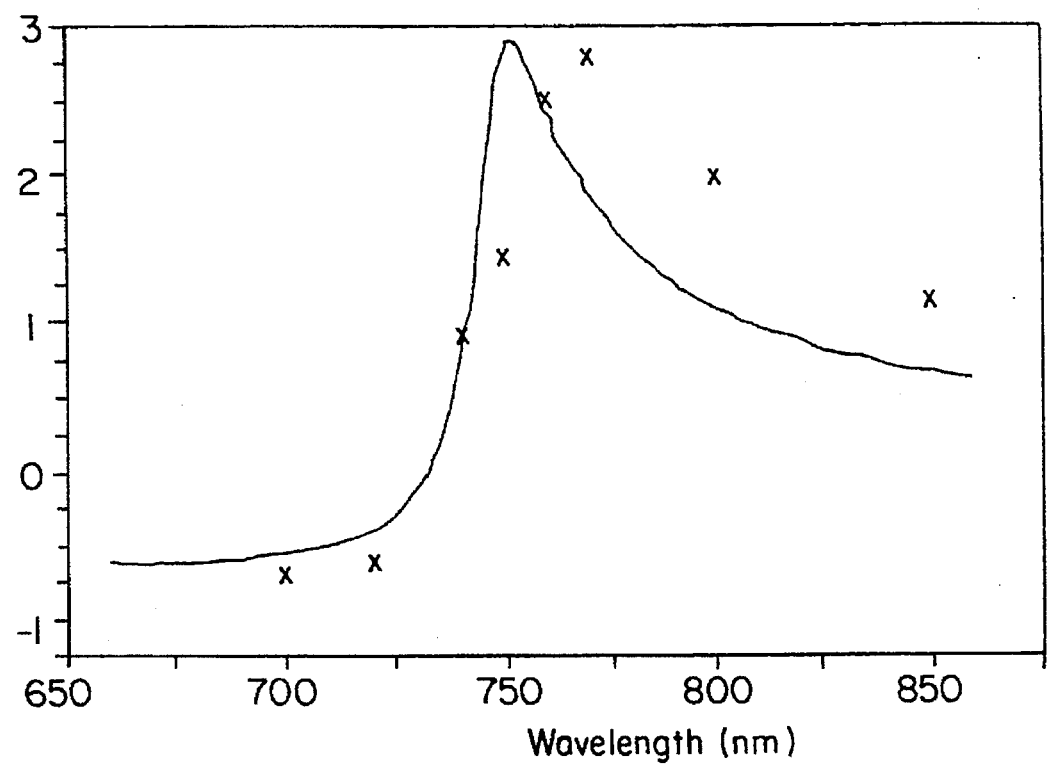

Reference will initially be made to FIG. 1 of the accompanying drawings, in which:

FIGS. 1A & 1B show two superposed diagrams representing the variation with wavelength for the absorptivity (top diagram) and refractive index (bottom diagram); and FIG. 2 is a diagram showing the theoretical (solid line) and experimental (x) refractive index spectrum of a dye solution.

As shown in FIG. 1, the refractive index maximum approximately corresponds to the maximum of the negative derivative of the absorptivity, and the refractive index minimum plateau lies in the vicinity of the maximum of the positive derivative of the absorptivity.

In the example illustrated in FIG. 1, the absorptivity graph has its maximum at 760 nm, and the width at half peak height is about 50 nm. The distance between maximum ($\lambda_1$) and minimum ($\lambda_2$) in refractive index will then also be about 50 nm. That is $\lambda_1$ is 785 nm and $\lambda_2$ is 735 nm.

Assume that the SPR sensing surface is first in contact with water. Since water has a certain normal dispersion in this range, –33 µRIU/nm (RIU=refractive index units) in the range 486–656 (slightly less at 760 nm), the refractive index difference over 50 nm will then be 1650 µRIU. (The constant influence of the sensing surface and optical system characteristics are neglected).

Then assume that all water is replaced by protein. For proteins the dispersion is herein roughly approximated to be –76 µRIU/nm, giving a refractive index difference over 50 nm of about 3800 µRIU. When protein is substituted for all water at the sensing surface, the refractive index difference between $\lambda_1$ and $\lambda_2$ will thus be changed from 1650 to 3800 µRIU, i.e. the difference will be 2200 µRIU. A conventional SPR response would, however, experience a substantially greater shift for this hypothetical case that all water is replaced by protein. Such a shift would correspond to the entire refractive index difference between protein and water, i.e. 1.55–1.33=0.22 RIU or 220000 µRIU. The refractive index difference measurement in accordance with the invention thus reduces the signal response for the binding of protein, analyte as well as non-specific material, to the sensing surface by a factor about 100.

For a dye it is quite different. As demonstrated in our international patent application WO 93/04357, the use of suitable dye or chromophoric labelling would give an at least about 25 times higher signal strength than proteins. The difference in signal strength between such a dye or chromophore and proteins would thus, considering the above shown attenuation of the protein response, amount to at least a factor 2500. Moreover, the signal emanating from protein adsorption can be further attenuated through a simple calibration procedure. First, the specific responses for protein adsorption (in the absence of chromophore) at the two wavelengths are determined, and a scale factor is calculated.

Secondly, when chromophore-labeled protein is adsorbed, the specific responses are scaled according to the obtained scale factor before the refractive index difference is calculated. In this manner the protein response can theoretically be reduced to zero.

As demonstrated above, the influence of non-specific binding to an SPR and related sensing surface is considerably reduced by proceeding in accordance with the invention. However, also the influences of the other limiting factors in SPR mentioned above will be heavily reduced as will be explained below.

For example, the variation of the background signal with time, e.g. due to variations in temperature, will not influence the measurement, as the refractive index difference is measured substantially simultaneously at the two respective wavelengths. One might thus say that there is an automatic baseline correction.

In summary, the invention provides for the combination of increased sensitivity (i.e. signal strength per quantity of analyte) with a substantial reduction of signal noise, the latter being defined in a broad sense to cover all types of measuring errors derived from any type of source of error. As is readily understood, the selectivity, i.e. the ratio of the signal generated by the desired chemical species and signal generated by non-desired chemical species (interferences, non-specific material) will be considerably increased.

It is, of course, possible to measure at more than two discrete wavelengths (for one and the same refractive index enhancing species). This would provide more information about the dispersion, and thereby a more robust interpretation of the detected signal, and the noise could be reduced by averaging the measurement results obtained.

Measuring the refractive index in rapid succession at a great number of wavelengths will produce a refractive index spectrum. In such a case the determined refractive index variation may be based upon measurement of the area under the spectrum graph rather than on the difference between the refractive indices at pairs of discrete wavelengths.

As mentioned above, it is also within the present inventive concept to measure the refractive index variation for a continuous wavelength range, covering the anomalous dispersion range of the refractive index enhancing species. In, for example, SPR measurement this will result in evaluating a change of the dip shape rather than the difference between two discrete dips.

The invention may be implemented in various ways.

In one embodiment of measuring at discrete wavelengths, the measurements are made at two time-resolved wavelengths. In the case of SPR, two time-resolved SPR intensity dip minima will then be obtained. For the evaluation thereof it is sufficient to determine the difference between the two dip minima. One way of achieving the desired time-resolution is using two light sources which are alternately turned on and off. A variation thereof is to use a broad wavelength light source in combination with two rotating high-pass/low-pass filters.

In another embodiment of measuring at discrete wavelengths, the measurements are performed at two wavelengths simultaneously. This may be accomplished by using two light sources which emit their light simultaneously. Alternatively, a light source having a broad wavelength range is combined with a filter excluding the central wavelength interval to produce two discrete emission peaks. In the case of SPR, two separate superposed SPR-dips will hereby be obtained. For the evaluation thereof different approaches may be used. In one approach, the width of the total dip is taken as a measure of the separation between the part-dips. Another approach is to separate the dips by fitting two dips of known shape. The distance between the minima of the two fitted dips is then a measure of the dip separation. Still another approach is analysis of the total graph shape by means of multivariate methods.

When measuring the variation for a continuous wavelength range, a broad emission wavelength range light source may be used, the emission maximum of which approximately matches the absorption maximum of the refractive index enhancing species and the emission spectrum of which is sufficiently broad to cover at least a major part of the anomalous dispersion range. In SPR measurement, quantitation of the response will then be based upon analysis of the shape of the response dip. In the simplest case, this may be performed by calculation of the dip width, whereas in other cases total graph shape analysis by multivariate techniques may be required.

As mentioned above, the measurements at discrete wavelengths should generally be performed at, or as close as possible to the maximum and minimum, respectively, of the refractive index with respect to wavelength. If, with regard to the maximum refractive index measurement, the wavelength is selected on the high wavelength side of the maximum of the refractive index, the distance between the measurement wavelength and said maximum should preferably be less than 100 nm (corresponding to a possible enhancement of at least about 5 times, on a mass basis, depending on the absorptivity), and more preferably, less than 50 nm (corresponding to a possible enhancement of at least about 10 times, on a mass basis, depending on the absorptivity). If, on the other hand, the measurement wavelength is selected on the low wavelength side of the maximum of the refractive index, the measurement wavelength must be very close to said maximum since the refractive index decreases rapidly with decreasing wavelength in this region.

In the case of the refractive index minimum measurement, on the other hand, the measurement wavelength is advantageously within the refractive index minimum plateau as explained above. Alternatively, the low refractive index measurement can be performed on the high wavelength side of the refractive index maximum. Since the refractive index decreases with wavelength in this region, a large refractive index difference can be obtained if the wavelength difference is sufficiently large. In this mode, the sensitivity enhancement will not be quite as large as if the low refractive index measurement is made near the refractive index minimum, but the noise reduction and the increased selectivity will still be obtained.

Further, the absorptivity (extinction coefficient) of the refractive index enhancing species should be as high as possible, preferably higher than $10 \text{ lg}^{-1} \text{ cm}^{-1}$, and more preferably higher than $20 \text{ lg}^{-1}\text{cm}^{-1}$.

By proper selection of the refractive index enhancing species or probe a very high refractive index may thus be obtained. Which specific measuring wavelength to choose for a specific index enhancing species or probe, or vice versa, will, of course, depend on inter alia the particular probe and may readily be established by the skilled person once he has had knowledge of the present invention.

For the purposes of the present invention the index enhancing species or probe preferably is or includes a dye or chromophoric molecule. Usually a dye molecule is conjugated to another molecule, such as a protein or polypeptide (e.g. an antibody or fragment thereof). Exemplary dyes are of the azine, thiazine, oxazine, cyanine, merocyanine, styryl, triphenylmethane, chlorophyll and phthalocyanine types.

The optochemical methods for which the present invention may be used are, as mentioned previously, not restricted to SPR methods, but extend to any assay method measuring a change of the refractive index as being indicative of the presence of an analyte. Such methods include both internal and external reflection methods, for example, ellipsometry, external Brewster angle reflectometry, and evanescent wave reflectometry, the latter including Brewster angle reflectometry, critical-angle reflectometry, SPR reflectometry, evanescent wave ellipsometry, scattered total internal reflection (STIR), optical waveguide sensors, refractometric optical fiber sensors, evanescent wave based imaging, such as critical angle resolved imaging, Brewster angle resolved imaging, SPR angle resolved imaging; etc.

The contact between the fluid sample medium and the optical surface may be static or, preferably dynamic, i.e. by providing the sensing surface or surfaces in some kind of flow cell.

Suitable assay formats for making use of the present invention include, but are, of course, not restricted thereto in any way, those described in the aforementioned WO 90/11525 and EP-A-276 142, including competition assays, displacement assays and sandwich type assays. In a competition assay the probe will compete with the analyte for the binding to the sensing surface, whereas in a displacement assay the probe is bound to the sensing surface and will be displaced by the probe. In a sandwich assay the probe is bound to the analyte, either before or after the latter is bound to the sensing surface.

A competition assay for, for instance a hapten, such as e.g. theophylline, may thus be performed by conjugating a suitable probe to theophylline, and measuring, at two wavelengths selected at or near the refractive index maximum and minimum, respectively, of the probe, the extent to which the sample, when mixed with the probe, influences, i.e. competes, with the binding of the conjugated theophylline to the sensing surface.

In order to demonstrate the feasibility of the assay method of the present invention, the following experiments were performed with a variable wavelength SPR-based biosensor instrument.

EXAMPLE 1

Variation of Refractive Index Increment With Wavelength For a Dye 1 mM of the dye HITC (1,1',3,3,3',3'-hexamethylindotricarbocyanine, 94% purity, Sigma H0387) was dissolved in a mixture of 50% ethanol and 50% citrate buffer (pH 3, 0.1M citrate, 0.4M NaCl, 0.05% Tween 20). The solution was continuously pumped over an SPR sensing surface (BIAcore™ Sensor Chip CM5, Pharmacia Biosensor AB, Uppsala, Sweden) mounted in a non-commercial SPR-instrument with a variable wavelength source. The wavelength was stepped from 700 to 850 nm, and the angle of the SPR light intensity minimum (Θ) was determined for each wavelength and compared to the angle when pure ethanol/buffer mixture was pumped over the surface.

The results are presented in Table 1 below. In Table 1, ΔΘ is the angle difference between solutions with and without HITC, and Δn is the difference in refractive index between solutions with and without HITC, calculated after refractive index calibration of the instrument with glycerol/water mixtures of known composition. DRIU=differential refractive index unit.

In FIG. 2, the Δn data are plotted against wavelength. The solid line represents a theoretical prediction (see C. F. Bohren, D. R. Huffman, "Absorption and scattering of light by small particles", John Wiley & Sons, New York, 1983, Chap. 9) of the refractive index as a function of wavelength, calculated from the measured absorption spectrum of the HITC solution (maximum absorptivity 260000 $M^{-1}$ $cm^{-1}$ at 743 nm). The qualitative agreement between theory and experiment is good, and maximum refractive index difference is obtained by choosing the two measurement wavelengths at about 700 and 770 nm, respectively.

TABLE 1

| Wavelength (nm) | Θ Buffer (°) | Θ HITC (°) | ΔΘ (°) | Δn (mDRIU) |
|---|---|---|---|---|
| 700 | 71.99 | 71.91 | −0.08 | −0.72 |
| 720 | 71.24 | 71.17 | −0.07 | −0.63 |
| 740 | 70.64 | 70.65 | 0.01 | 0.90 |
| 750 | 70.35 | 70.51 | 0.16 | 1.44 |
| 760 | 70.01 | 70.29 | 0.28 | 2.51 |
| 770 | 69.87 | 70.18 | 0.31 | 2.78 |
| 800 | 69.21 | 69.43 | 0.22 | 1.98 |
| 850 | 68.41 | 68.54 | 0.13 | 1.17 |

EXAMPLE 2

Measurement of Bulk Refractive Index Increment Using the Differential Method A citrate buffer (pH 3, 0.1M citrate, 0.4M NaCl, 0.05% Tween 20) was prepared and mixed with equal amounts of spectrographically pure ethanol. 1.0 mM of the dye HITC (same quality as in Example 1) was dissolved in an aliquot of the citrate/ethanol-mixture. Then, sucrose (pro analysi, dried) was carefully weighed and dissolved to concentrations of 0%, 0.8%, 1.6% and 3.2% in citrate/ethanol, and in HITC/citrate/ethanol.

Absorption spectra in the region 500–900 nm were recorded for HITC+0% sucrose and for HITC+1.6% sucrose, after dilution to 4 µM with citrate/ethanol. The two spectra were practically identical: max 743.2 nm, Amax 1.062 for HITC+0% sucrose, and max 742.8 nm, Amax 1.053 for HITC+1.6% sucrose. Thus, the addition of sucrose did not change the spectral properties of HITC.

SPR-measurements were performed on an SPR-sensing surface (BIAcore™, Sensor Chip CM5, Pharmacia Biosensor AB, Uppsala, Sweden) mounted in the same instrument as in Example 1. All measurements were made at two wavelengths. The samples were continuously pumped over the surface in sequence, and the wavelength setting was quickly shifted between 700 and 770 nm for each sample. The instrument is a non-commercial and flexible research instrument, but has got rather poor precision (e.g. manual wavelength-setting), so first the repeatability of the wavelength shifts was determined. Citrate/ethanol was pumped over the surface, and the wavelength was shifted between 700 and 770 nm ten times.

The mean of the difference between 700 and 770 nm was 20753 mpixel (mpixel is here an uncalibrated angle unit) with a standard deviation of 112 mpixel.

Then, citrate/ethanol with 0–3.2% sucrose was pumped over the surface two times, and readings at 700 and 770 nm were made to obtain calibration graphs (to translate mpixel at each wavelength to Refractive Index Units, RIU). The slopes of the fitted straight lines at 700 and 770 nm were not significantly different, so in subsequent experiments no calibration was performed, but mpixel-values were used as such. The mean slope of the calibration graphs was 1337 mpixel/(% sucrose).

Then, HITC/citrate/ethanol with 0–3.2% sucrose was pumped over the surface two times, and readings at 700 and 770 nm were made. To minimize the drift (e.g. due to temperature changes) all values were taken as differences to a recent reading for pure citrate/ethanol. The results are presented in Table 2.

TABLE 2

| Sucrose conc. (%) | 770 nm (mpixel) | 700 nm (mpixel) | Diff. 770–700 nm (mpixel) |
| --- | --- | --- | --- |
| 0   | 2394 | −1014 | 3408 |
| 0.8 | 3442 | 126   | 3316 |
| 1.6 | 4531 | 1442  | 3089 |
| 3.2 | 6711 | 3586  | 3125 |

The overall mean of the difference between the readings at 770 and 700 nm is 3235 mpixel, and the standard deviation is 153 mpixel. This standard deviation is not significantly different from the value 112 mpixel obtained in the repeatability experiment, so no difference between the four values are shown. Neither is there any significant trend of the mpixel-values with respect to sucrose concentration. This experiment demonstrates that, by taking the difference of the responses at two different wavelengths, the influence of variations in absolute refractive index can be cancelled out, and only the differential contribution from the dye molecules is obtained.

EXAMPLE 3

Assay for Theophylline Using the Differential Method

The dye I (1,1'-(4-sulfobutyl)-3,3,3',3'-tetramethyl-6-carboxymethylindotricarbocyanine) was synthesized according to P. L. Southwick et al., Cytometry, 11 (1990) 418, dye XVIII. This dye is a water-soluble and reactive derivative of the dye HITC used in the previous examples. The absorption maximum in water was at 746 nm. The dye I was activated with TSTU (O-(N-succinimidyl)-N,N,N',N'-tetramethyluronium tetrafluoroborate, Fluka, Switzerland) and dissolved in borate buffer (pH 8.5, 0.1M borate) containing aminotheophylline (8-(3-aminopropyl) theophylline). The reaction yielded a clear solution. Thin layer chromatography confirmed that the aminotheophylline was completely used up. The absorption spectrum of the reaction mixture was similar to that of pure dye I. In subsequent experiments, the reaction mixture was used without further purification.

These experiments were run on the same non-commercial SPR-instrument as in the previous examples. First, two Sensor Chips were mounted (in sequence) in the instrument, and the baseline level in the presence of buffer was read at 700 and 770 nm. Then, four Sensor Chips with immobilised anti-theophylline-antibody were mounted (in sequence), and the baseline read in the same way. The mean difference in the baseline for Sensor Chips with and without antibody was 12203 mpixel at 700 nm and 8269 mpixel at 770 nm. So, the scale factor with respect to protein uptake was 8269/12203= 0.68 with an RSD of 2%. This is in reasonable agreement with the theoretically obtained value of 0.76.

Solutions of the conjugate of dye I-aminotheophylline (approx. 35 µM) were pumped over two Sensor Chips with immobilised anti-theophylline antibodies for three minutes, and after a further five minutes the response was read at 700 and 770 nm. The mean of the response was −150 mpixel at 700 nm and +430 mpixel at 770 nm (after division with the scale factor 0.68), so the mean difference was 580 mpixel. This experiment demonstrates that the differential method can equally well be applied to binding of molecules to the surface.

Then the same experiment was repeated with addition of 2 µg/ml of rabbit anti-mouse Fc to the solution of dye I-aminotheophylline. The antibody is meant to simulate "non-specific binding" in a realistic assay. From control experiments, this concentration of antibody is expected to give rise to an uptake of 100–200 mpixel, but in the present experiment it was difficult to determine the exact amount due to temperature drift (because of the manual operation of the instrument a few minutes elapsed between each angle reading). The mean difference between the response at 770 and 700 nm, respectively, was 560 mpixel, which was not significantly differently from the value 580 mpixel in the previous experiment. This experiment demonstrates that the differential method can cancel out the contribution from non-specific binding of proteins.

Furthermore, the standard deviation between pairwise uptake readings (mean of 2–3 readings) at one single wavelength in the two experiments was 130 mpixel. The standard deviation of pairwise differences between 700 and 770 nm was only 77 mpixel, most of which is thought to be contributed by the wavelength shifts. (With randomly distributed values, the standard deviation would have risen by a factor of $\sqrt{2}$, to 180 mpixel, for the differences.) Due to the small samples this difference in standard deviations is not statistically significant, but an indication of the increased precision of the differential method is seen.

The invention is, of course, not restricted to the embodiments specifically described above, but many changes and modifications may be made within the general inventive concept as defined in the following claims.

I claim:

1. A method for assaying for an analyte in a fluid sample comprising,
   measuring a change in refractive index at a solid optical surface in contact with the sample, wherein said change is caused by the analyte affecting the binding or release of a refractive index changing species to or from the optical surface, wherein the refractive index of said refractive index enhancing species varies with wavelength;
   determining the variation with wavelength of said change of refractive index caused by the variation of refractive index with wavelength of said refractive index enhancing species, for a number of discrete wavelengths or for a continuous range of wavelengths; and
   correlating said variation to the amount of analyte in said fluid sample.

2. The method according to claim 1, wherein said determined variation is the change in the refractive index difference between refractive indices of the refractive index enhancing species measured at two different wavelengths.

3. The method according to claim 2, wherein one measuring wavelength is selected at or near the refractive index maximum of said refractive index enhancing species.

4. The method according to claim 2 or 3, wherein one measuring wavelength is selected at or near the refractive index minimum plateau of said refractive index enhancing species on the low wavelength side of the refractive index maximum.

5. The method according to claim 2 or 3, wherein one measuring wavelength is selected on the high wavelength side of the refractive index maximum.

6. The method according to claim 3, wherein when said measurement wavelength is on the high wavelength side of said maximum, the distance between the measurement wavelength and said maximum is less than 100 nm, preferably less than 50 nm, and that when said measurement wavelength is on the low wavelength side, the measurement wavelength is close to said maximum.

7. The method according to claim 1, wherein said determination comprises determining the variation of the refractive index with wavelength at more than two wavelengths.

8. The method according to claim 1, wherein said determination comprises determining the variation of the refractive index with wavelength for a continuous range of wavelengths.

9. The method according to claim 1, wherein said refractive index enhancing species comprises a protein or polypeptide conjugated to a chromophore or dye and wherein said protein or polypeptide is capable of specifically interacting with said analyte.

10. The method according to claim 1, wherein said refractive index enhancing species comprises a hapten conjugated to a chromophore or dye and wherein said hapten is capable of specifically interacting with said analyte.

11. The method according to claim 1, wherein said determination is based upon internal reflection, particularly surface plasmon resonance.

12. The method according to claim 1, wherein said determination is based upon external reflection.

13. The method according to claim 1, wherein said method is an assay selected from the group consisting of competition assays, displacement assays and sandwich assays.

14. The method according to claim 1, wherein said method is an immunoassay.

* * * * *